United States Patent [19] [11] 4,060,088
Morrison, Jr. et al. [45] Nov. 29, 1977

| [54] | ELECTROSURGICAL METHOD AND APPARATUS FOR ESTABLISHING AN ELECTRICAL DISCHARGE IN AN INERT GAS FLOW |
|---|---|
| [75] | Inventors: Charles F. Morrison, Jr.; Frank W. Harris; Michael D. Patzer, all of Boulder, Colo. |
| [73] | Assignee: Valleylab, Inc., Boulder, Colo. |
| [21] | Appl. No.: 649,725 |
| [22] | Filed: Jan. 16, 1976 |
| [51] | Int. Cl.² .............................................. A61B 17/36 |
| [52] | U.S. Cl. ............................ 128/303.17; 219/121 P |
| [58] | Field of Search .................... 128/303.17, 303.14, 128/303.13, DIG. 22, 405, 404, 303.1; 219/121 P, 75, 121 R |

[56] References Cited

U.S. PATENT DOCUMENTS

| 3,434,476 | 3/1969 | Shaw et al. ....................... 128/303.1 |
| 3,569,661 | 3/1971 | Ebeling ............................. 219/121 P |
| 3,692,973 | 9/1972 | Oku et al. ......................... 219/121 P |
| 3,699,967 | 10/1972 | Anderson ......................... 128/303.14 |
| 3,832,513 | 8/1974 | Klasson ........................ 219/121 P X |

OTHER PUBLICATIONS

"RF and Laser Combine to Provide High-Energy Beam", *Machine Design*, Nov. 27, 1975.

*Primary Examiner*—Robert W. Michell
*Assistant Examiner*—Michael H. Thaler
*Attorney, Agent, or Firm*—Gerald J. Ferguson, Jr.; Joseph J. Baker

[57] ABSTRACT

An electrosurgical method and apparatus for coagulating by fulguration where the electrical discharge is established through a formation of flowing inert gas where the formation may either be a diffuse blanket of the flowing gas or a well defined column thereof.

17 Claims, 5 Drawing Figures

ELECTROSURGICAL METHOD AND APPARATUS FOR ESTABLISHING AN ELECTRICAL DISCHARGE IN AN INERT GAS FLOW

RELATED APPLICATIONS

This application is related to a first U.S. patent application Ser. No. 649,683 filed on Jan. 16, 1976 by Charles F. Morrison, Jr. and Benson C. Weaver, entitled "Electrosurgical Method and Apparatus for Initiating an Electrical Discharge in an Inert Gas Flow" and a second U.S. patent application Ser. No. 649,682 filed on Jan. 16, 1976 by Charles F. Morrison, Jr., entitled "Improved Electrosurgical Method and Apparatus for Initiating an Electrical Discharge in an Inert Gas Flow", all of the foregoing applications being assigned to the same assignee.

BACKGROUND OF THE INVENTION

1. Field of the Invention

This invention relates to electrosurgery and in particular an electrosurgical method and apparatus for coagulating by fulguration.

2. Discussion of the Prior Art

Electrosurgical coagulation by fulguration consists of the establishment of electrical discharges to body tissue with bursts of radio-frequency energy. It is used to dehydrate, shrink, kill, or char the tissue. This is most often to stop bleeding and oozing, or to otherwise seal the tissue. Conventional fulguration techniques are complicated by the following:

1. Very high voltages are required to start and maintain the high crest factor sparking needed for effective fulguration. Few solid state electrosurgical generator systems can provide the output parameters needed for truly satisfactory performance. Sparks are typically short and hard to start and control.

2. With high voltage and crest factor, as provided by conventional generators, the precise control of the fulguration site is impossible due to the "arc" nature of the discharge. The spark does not issue from the point of the electrode in the direction indicated, but arcs from the side of the point in a curved trajectory to nearby flesh. The spark wanders increasingly with greater spark length. Fulguration at the bottom of a hole or crevice is especially difficult to achieve.

3. Should the electrode accidentally touch the tissue, the partially dehydrated tissue can often adhere to the hot electrode and be inadvertently ripped away creating unnecessary complications. In addition to surgical complications, such sticking fouls the electrode such that it must be scraped clean before continuing the operation.

4. Conventional fulguration systems cannot be used to quickly treat large areas of bleeding or oozing flesh.

5. Considerable volumes of dense unpleasant smoke and fumes are produced.

SUMMARY OF THE INVENTION

With this invention, the above difficulties can be totally eliminated. In particular, a primary object of this invention is the provision of an electrosurgical method and apparatus for coagulating by fulguration where the electrical discharge is established through a formation of flowing inert gas where the formation may either be a diffuse blanket of the flowing gas or a well defined column thereof.

These and other objects of the invention will become apparent from a reading of the following specification and claims taken together with the drawing.

DETAILED DESCRIPTION OF THE PREFERRED EMBODIMENTS OF THE INVENTION

Figure 1:
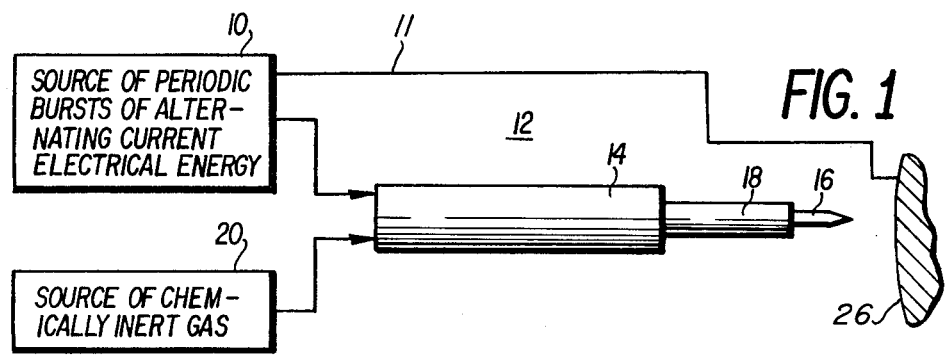
FIG. 1 is an illustrative schematic diagram of apparatus in accordance with the invention.

Referring to the figures of the drawing where like reference numerals refer to like parts and, in particular, referring to FIG. 1, there is shown a source 10 of electrical energy which may be continuous or preferably discontinuous such as periodic bursts of electrical energy such as illustrated in FIG. 7 of U.S. Pat. No. 3,699,967 granted to Robert K. Anderson. This energy is typically in the high frequency range — that is, about 200 kHz or higher. The wave form has a high crest factor — that is, typically 5–10 where the crest factor of a periodic function is the ratio of its crest (peak maximum) value to its root-mean-square value. The bursts may occur at a repetition rate of 15,000 to 50,000 bursts per second while the duration of each burst may consist of 1 to 5 cycles of the high frequency energy, it being understood that none of the foregoing values is critical. Such waveforms are well known for use as coagulating waveforms in electrosurgery. Source 10 is connected to an electrosurgical instrument generally indicated at 12. Instrument 12 basically comprises a support member 14, which may function as a handle. Member 14 supports an electrode 16, which may be directly supported by member 14 or indirectly supported thereby via an intermediate member 18, although intermediate member 18 does not necessarily also have to be employed as a support member, as will be described in more detail hereinafter. Source 10 may be electrically connected in a conventional manner to electrode 16 by appropriate connections (not shown) internal to members 14 and 18. As can be seen in FIG. 1, a return path 11 is provided from tissue 26 to source 10.

A source 20 of gas is also connected to instrument 12 and, as will be described in more detail hereinafter, the gas is employed to support an electrical discharge used for tissue coagulation and the like. The gas should be inert in the sense that it is not combustible by the electrical discharge nor will it support combustion of the electrode 16. It may, for example, be selected from the group consisting of nitrogen and the noble gases and mixtures thereof. Helium has been found to be particularly advantageous especially with respect to initiation of the electrical discharge, as will be discussed further hereinafter.

Figure 2:
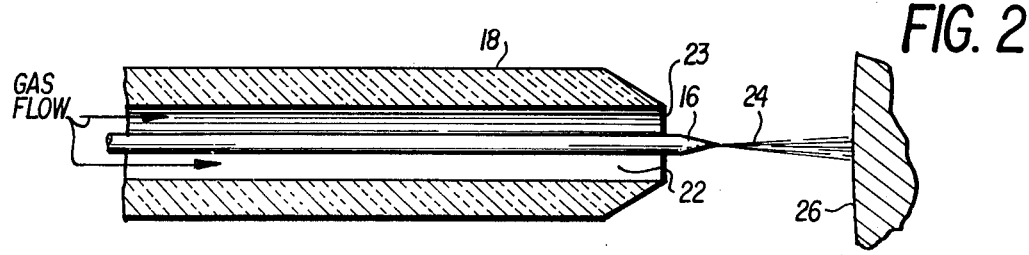
FIGS. 2–4 are cross-sectional views of various illustrative electrode structures in accordance with one aspect of the invention wherein a column of gas is formed.
Figure 3:
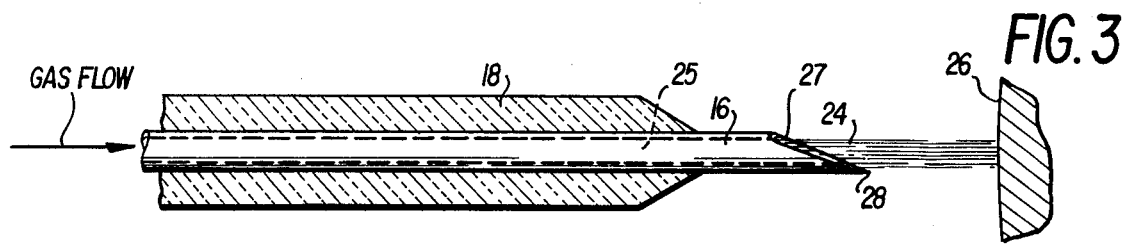
Figure 4:
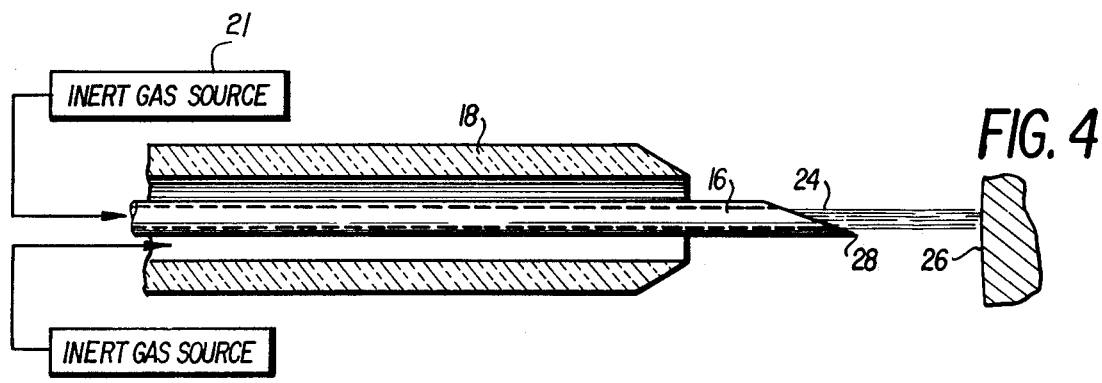

In FIGS. 2–4 there are shown electrode structures generally corresponding to that shown in FIG. 1. In FIG. 2, intermediate member 18 comprises a hollow tube disposed about and surrounding electrode 16 whereby an annular passageway 22 is provided through which the gas from source 20 flows. The tube has as opening 23, the area of which is preferably the same as the cross-sectional area of passageway 22 although advantageous results are obtained whenever the gas flow is focused. Thus, the exit from passageway 22 may also be cone shaped with the cone gently flaring inwardly to the end of passageway 22. Hence, as the gas flows out of opening 23, an outwardly extending, focused formation (as opposed to a diffuse formation) such as a column or cone of inert gas is formed adjacent the tip or end of electrode 16 to thereby facilitate the establishment and maintenance of a highly directive discharge 24 to a surface such as body tissue or the like. The active electrode is electrically conductive and typically may be made from tungsten, stainless steel, etc., while the tube 18 may be made from an electrically insulative material. The radial distance between electrode 16 and tube 18 may typically be about 30 mils while the diameter of electrode 16 is typically about 12–15 mils, it being understood that none of the foregoing values is critical to the desired formation of a column of gas.

The outwardly extending column of inert gas is well defined and produces a very long electrical discharge. This discharge is four to six times the length of that generated under the same conditions without the gas. The discharge is straight down the gas column. The directivity of the discharge is such that it can be directed to the bottom of a fissure or crevice without deflecting to the sides thereof and thus, is a very important aspect of the invention.

In FIG. 3, the electrode 16 comprises a hollow tube having a passageway 25 for the inert gas. The tube is truncated at the end thereof to form an opening 27 having an inside diameter of typically about 15–60 mils internal diameter, it being understood that the foregoing values are not critical to the desired formation of a column of gas. A sharp point 28 results due to the truncation of tube 16. Intermediate member 18 comprises a coating disposed on electrode 16 where preferably the coating is made of electrically insulating material. The gas flows through the electrode, cooling it very effectively, while providing the conduction column to the flesh. This arrangement provides excellent fulguration, but eventually the sharp point 28 tends to burn away. Directability is excellent, but spark length is less with this arrangement than with those of FIGS. 2 and 4.

In FIG. 4, the arrangements of FIGS. 2 and 3 are combined whereby gas flows through tubes 16 and 18. Preferably different gas flow rates are established in tubes 16 and 18. This can be effected by the employment of an additional gas source 21 or appropriate means (not shown) can be employed in the line from source 20 to effect the desired flow rates in tube 16 and 18 where the flow velocity in tube 16 may typically be about five times that in tube 18. This embodiment performs very well. The gas flow down center tube 16 provides directionality. It flows gently down outer tube 18 to prevent oxidation of the inner tube and to give additional gas column diameter. This enhances the the length of the discharge with respect to that obtainable in the FIG. 3 embodiment.

Further, it is also preferable to employ different gases in tubes 16 and 18 where the gas in center tube 16 discharges more readily than that in tube 18 to thereby enhance the effectiveness and directivity of the discharge. Thus, argon as the center tube gas and nitrogen as the outer tube gas provides a better focus and directability than the use of argon in both streams. Also, for example, argon in the outer tube and helium in the inner tube focuses better than helium in both channels.

In FIGS. 2–4 embodiments, the gas flow rate typically established in tube 18 in FIG. 2, tube 16 in FIG. 3, and tube 16 in FIG. 4 is about 0.02 standard cubic feet per minute while pressure of the gas in the column at the tissue is about 0.25 p.s.i. although it is to be understood that these values are not critical. Although electrode 16 is preferably pointed in FIG. 2 and preferably has a sharp point 28 in FIGS. 3 and 4 in order to facilitate initiation of the electrical discharge, it has been determined that when helium is used as the inert gas, electrode 16 may be non-pointed. Thus, for example, a perpendicularly cut-off tube of small diameter (32 mils, e.g.) may be used as electrode 16 where the discharge is essentially self-starting in helium after several touchdown starts.

The fulguration provided by all of the devices of FIGS. 2–4 is excellent when used with practically all electrosurgical generators, including solid state generators. The electrical discharge is typically $\frac{3}{8}$ to $\frac{3}{4}$ inches in length, making it easy to control. Precise control of the fulguration site is provided by the spark being straight and in the directed, columnated gas stream. The spark is easily directed to the bottoms of holes and crevices. It is not deflected to adjacent conducting structures as is the case in the absence of a gas flow pattern. Because of the long, electrical discharge there is little danger of accidentally touching the tissue with the discharging tip. In any event, very little of the tip is sufficiently hot to stick to the flesh, in that the gas flow keeps the structure very cool compared with other electrosurgical electrodes. In the columnar flow systems of FIGS. 2–4, the electrical discharge covers a well defined area, and can be swept across the tissue to provide rapid coverage of wide areas. Thus, such systems are many times as effective (for many applications) as the same generator with a conventional electrode. In addition, the quantity of smoke and fumes generated is an order of magnitude less than with prior art arrangements.

Figure 5:
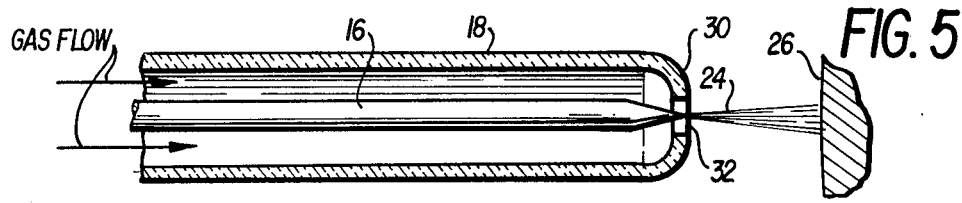
FIG. 5 is a cross-sectional view of an illustrative electrode structure for use with the arrangement of FIG. 1 in accordance with a further aspect of the invention wherein a blanket of gas is formed.

In FIG. 5, there is illustrated a method for producing coagulation by fulguration where a diffuse blanket of inert gas is formed between electrode 16 and tissue 26 as opposed to a focused formation such as the column of inert gas formed by the embodiments of FIGS. 2–4. The configuration of the instrument of FIG. 5 corresponds to that of a typical thermal-inert-gas (TIG) welder; however, it is employed for tissue coagulation in accordance with one aspect of the invention. As can be appreciated, the electrically insulated cover has a turned-in portion 30 with an opening 32 disposed therein. Thus, the gas which flows through the annular space between electrode 16 and 18 encounters portion 30 and eventually is diffused out opening 32 to form a a diffuse blanket (as opposed to a column) of the inert gas between the electrode and the tissue. As indicated hereinbefore with respect to FIGS. 2–4, there is preferably little, if any, obstacle such as end portion 30 in the gas flow paths in the embodiments of these figures. Rather, the area of opening 27 of tube 16 in FIGS. 3 and 4 and the area of opening 23 of tube 18 in FIGS. 2 and 4 are preferably, substantially the same as the cross-sectional areas of passageway 25 and passageway 22, respectively. Hence, the establishment of a column of gas occurs in the embodiments of FIGS. 2 through 4. Thus, the discharge established by the embodiments of these figures is both long and directed while that of the FIG. 5 embodiment is long but not directed due to the diffuse nature of the gas blanket. Nevertheless, the FIG. 5 embodiment is useful in many electrosurgical, coagulation applications due to the discharge length, as will be discussed further hereinafter.

In welding applications, the gas blanket established by a TIG welder provides two functions. First, it provides an inert cover for the hot welding tip and the heated work piece such that oxygen is excluded, preventing corrosion. Second, it provides a medium in which a gaseous discharge can be readily initiated, by application of an essentially continuous wave, radio frequency (RF) power. Once the discharge is initiated, the RF power is turned off so that thereafter only a low frequency or DC current is applied to the electrode. Thus, the discharge initiated by the RF power permits striking of the low voltage welding arc without the electrode touching the work piece. If applied to living tissue, the low frequency or DC welding current could cause fibrilation and death if its driving voltage were sufficiently high. The raw blast of RF voltage used to start the welding arc is not suitable for either welding or fulguration.

Hence, in accordance with a further aspect of this invention, the TIG welder configuration of FIG. 5 is employed for electrosurgical coagulation by applying to the instrument either continuous wave electrical energy or periodic blasts of high frequency, electrical energy, such as produced by source 10 of FIG. 1. The source 10 output is employed as long as an electrical discharge takes place between electrode 16 and tissue 26 of FIG. 5, as opposed to the welding arrangement where the RF power is applied only during the time interval necessary to initiate the arc.

The FIG. 5 embodiment is somewhat limited, due in part to the diffuse nature of the gas flow, and in part due to the vaporized materials issuing from the flesh which contaminate the gas. In spite of this, the application of this embodiment provides spark length and fast wide coverage not available with conventional electrosurgical tools.

The embodiments of FIGS. 2, 3 and 5 are also advantageous in that the primary electrical discharge from the tip of electrode 16 can be readily initiated. In particular, whenever a person such as a doctor grips the instrument and, for example, places his finger on tube 18, an auxiliary electrical discharge will be established between the interior of tube 18 and electrode 16. The auxiliary discharge results from the electric field established between the doctor's finger and the active electrode 16 where the latter two will be at different electric potentials depending on various factors such as the magnitude of the voltage on electrode 16, the thickness of tube 18, etc. Tube 18 should be electrically insulative and preferably thick enough to prevent discomfort to the doctor while thin enough to permit establishment of the auxiliary discharge. The auxiliary discharge will be spaced from the electrode tip a certain distance depending on where the doctor places his finger. It is thought that the ions generated in the auxiliary electrical discharge are swept by the flowing gas to the electrode tip to initiate the primary discharge at the tip although there is no intent to be limited to a particular theory of operation.

What is claimed is:

1. An electrosurgical apparatus for producing coagulation of tissue by fulguration comprising
    a support;
    a tubular electrode supported by said support and outwardly extending therefrom;
    a source of inert gas connected to said tubular electrode, said inert gas flowing through said tubular electrode and outwardly therefrom to thereby facilitate the establishment of an electric discharge in the inert gas extending outwardly from the tubular electrode;
    generator means for applying high frequency, electrical energy to said electrode; and
    means for returning said electrical energy from said tissue to said generator means.

2. Apparatus as in claim 1 where said high frequency is at least 200 kHz.

3. Apparatus as in claim 1 including an electrically insulative covering disposed on the outer surface of said tubular electrode, said tubular electrode being truncated at the end thereof to form a sharp point.

4. Apparatus as in claim 1 including a hollow tube disposed about said tubular electrode, said inert gas flowing through both said hollow tube and said tubular electrode and outwardly therefrom.

5. Apparatus as in claim 4 where said hollow tube is electrically insulative and said tubular electrode being truncated at the end thereof to form a sharp point.

6. Apparatus as in claim 4 including means for producing different flow velocities of said inert gas in said hollow tube and said tubular electrode, the flow velocity in said tubular electrode being substantially greater than that in said hollow tube.

7. Apparatus as in claim 4 including means for respectively providing first and second inert flowing gases in said hollow tube and said tubular electrode where electrical discharge is more readily established in said second gas than in said first gas.

8. An electrosurgical apparatus as in claim 4 where said hollow tube is electrically insulative.

9. Apparatus as in claim 1 where said inert gas is selected from the group consisting of nitrogen, the noble gases and mixtures thereof.

10. Apparatus as in claim 9 where said inert gas is selected from the group consisting of nitrogen, helium, argon, neon and mixtures thereof.

11. Apparatus as in claim 10 where said inert gas is helium.

12. An electrosurgical apparatus as in claim 1 where said generator means includes means for applying said high frequency, electrical energy in periodic bursts.

13. An electrosurgical method for coagulating tissue by fulguration with an instrument comprising a support; and a tubular electrode supported by said support and outwardly extending therefrom, said method comprising the performance of the following steps in any order,
    directing inert flowing gas through said tubular electrode and outwardly therefrom to thereby facilitate the establishment of a directional electric discharge in said gas,
    positioning the instrument adjacent to the tissue to be coagulated; and
    applying high frequency electrical energy to said electrode as long as an electric discharge takes place between said electrode and said tissue thereby effecting said coagulating of the tissue.

14. A method as in claim 13 where said electrical energy is applied in periodic bursts.

15. A method as in claim 13 where said high frequency is at least 200 kHz.

16. A method as in claim 13 where said electrical energy is the only energy utilized to effect said coagulating of the tissue.

17. An electrosurgical method for coagulating tissue by fulguration with an instrument comprising a support; a tubular electrode supported by said support and outwardly extending therefrom; and a hollow, electrically insulative tube disposed about said electrode and supported by said support, said method being performed by a person and comprising the steps of directing inert flowing gas through said tubular electrode and said electrically insulative tube and outwardly therefrom;

applying high frequency electrical energy to said electrode; and said person gripping said instrument and placing a finger on said tube and positioning the instrument adjacent the tissue to be coagulated whereby an auxiliary electrical discharge is established between the inner surface of said electrically insulative tube and said tubular electrode to thereby initiate a primary electrical discharge from the end of the electrode to said tissue and hence effect the coagulation thereof.

* * * * *